(12) United States Patent
Reed

(10) Patent No.: US 6,800,079 B2
(45) Date of Patent: Oct. 5, 2004

(54) ORTHOPEDIC STABILIZATION DEVICE AND METHOD

(75) Inventor: Gary J. Reed, Turlock, CA (US)

(73) Assignee: LOck-N-Stitch, Inc., Turlock, CA (US)

( * ) Notice: Subject to any disclaimer, the term of this patent is extended or adjusted under 35 U.S.C. 154(b) by 0 days.

(21) Appl. No.: 10/099,400

(22) Filed: Mar. 15, 2002

(65) Prior Publication Data

US 2003/0176861 A1 Sep. 18, 2003

(51) Int. Cl.⁷ .............................................. A61B 17/56
(52) U.S. Cl. ......................................... 606/73; 606/61
(58) Field of Search ........................... 606/63, 73, 104, 606/61, 72; 411/354, 178, 411, 424

(56) References Cited

U.S. PATENT DOCUMENTS

| | | | | |
|---|---|---|---|---|
| 4,175,555 A | * | 11/1979 | Herbert | 606/73 |
| 4,177,524 A | * | 12/1979 | Grell et al. | 606/86 |
| 4,648,388 A | * | 3/1987 | Steffee | 606/61 |
| 5,019,079 A | * | 5/1991 | Ross | 606/72 |
| 5,499,892 A | * | 3/1996 | Reed | 411/5 |
| 5,536,127 A | * | 7/1996 | Pennig | 411/413 |
| 5,584,834 A | * | 12/1996 | Errico et al. | 606/61 |
| 5,586,984 A | * | 12/1996 | Errico et al. | 606/61 |
| 5,667,508 A | * | 9/1997 | Errico et al. | 606/73 |
| 5,669,911 A | * | 9/1997 | Errico et al. | 606/61 |
| 5,733,286 A | * | 3/1998 | Errico et al. | 606/61 |
| 5,800,107 A | * | 9/1998 | Giannuzzi et al. | 411/386 |
| 5,899,906 A | * | 5/1999 | Schenk | 606/73 |
| 5,989,254 A | * | 11/1999 | Katz | 606/73 |
| 6,053,916 A | * | 4/2000 | Moore | 606/61 |
| 6,435,788 B2 | * | 8/2002 | Reed | 411/178 |
| 6,454,768 B1 | * | 9/2002 | Jackson | 606/61 |
| 6,572,315 B1 | * | 6/2003 | Reed | 411/307 |

* cited by examiner

Primary Examiner—Pedro Philogene
Assistant Examiner—David A Bonderer
(74) Attorney, Agent, or Firm—Bernhard Kreten & Assoc.

(57) ABSTRACT

An orthopedic stabilization structure including a threaded fastener capable of articulation to accommodate various skeletal geometries, a rod, and a cup supporting the threaded fastener and the rod to be subsequently held in fixed position with respect to the skeletal structure.

5 Claims, 12 Drawing Sheets

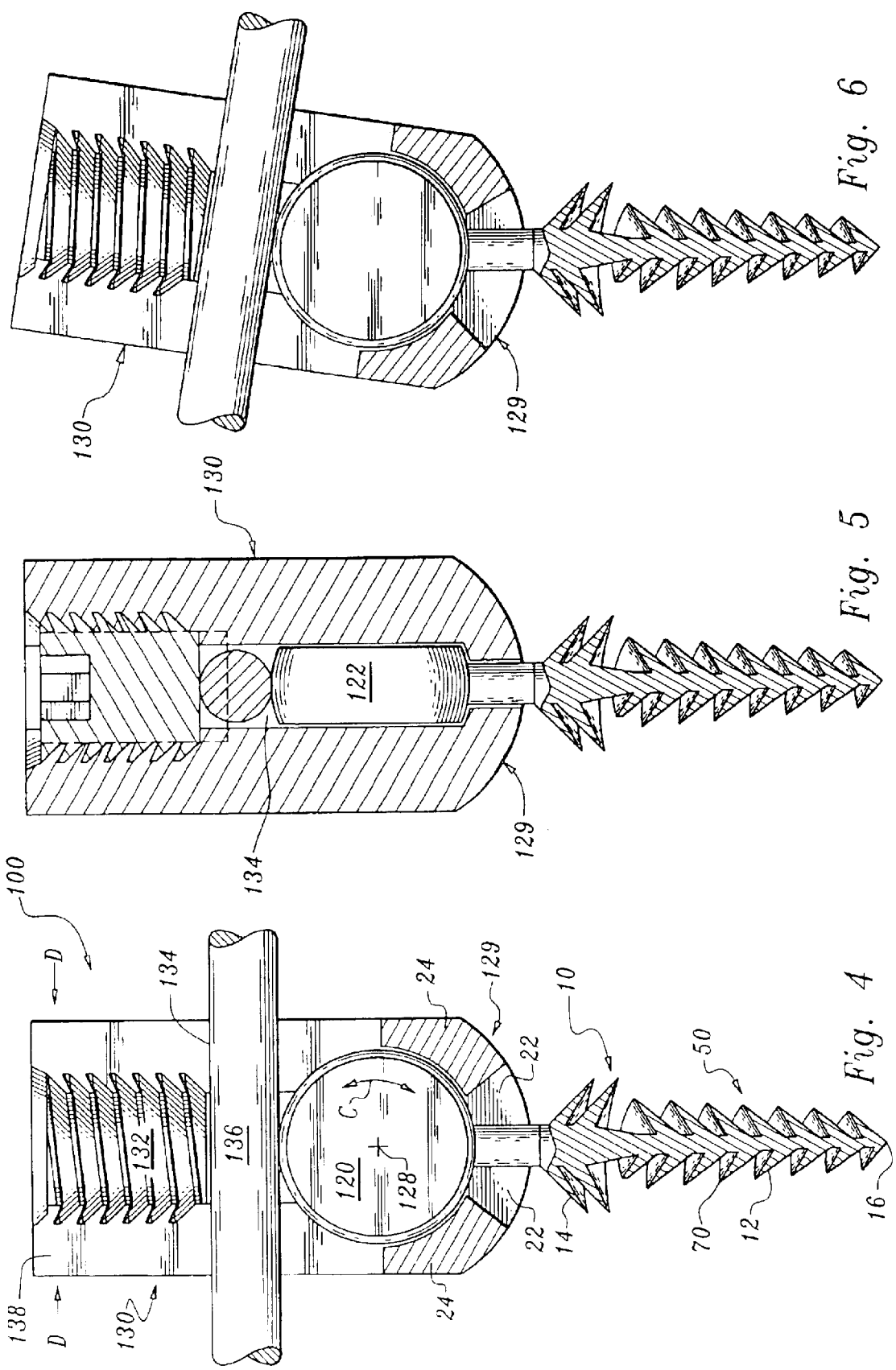

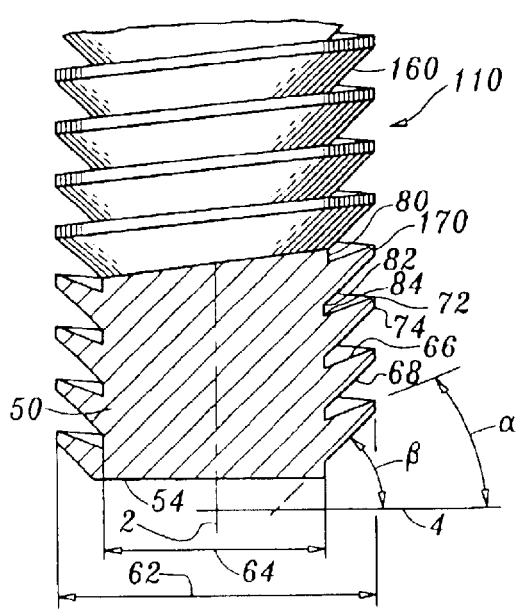
Fig. 7
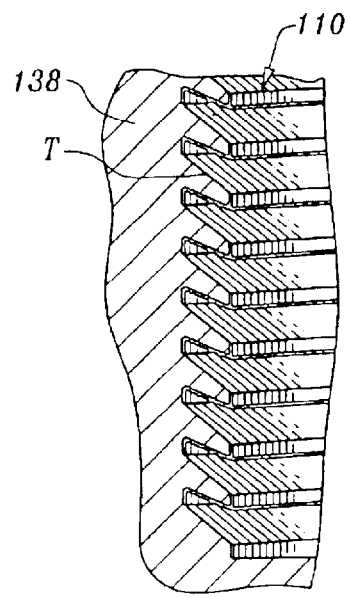
Fig. 8
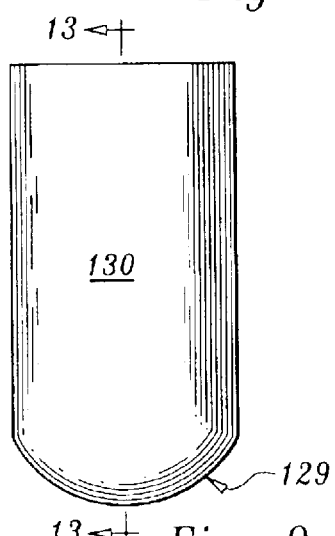
Fig. 9
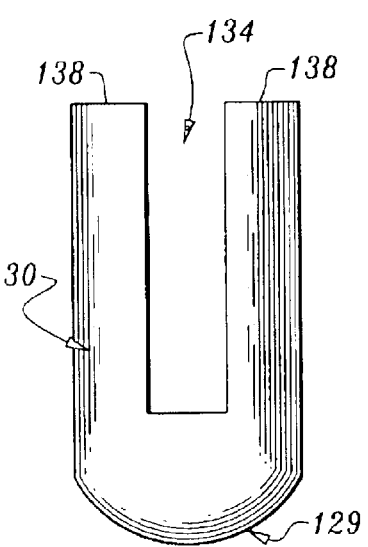
Fig. 10
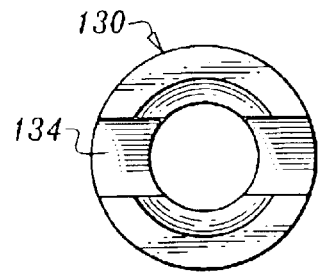
Fig. 11
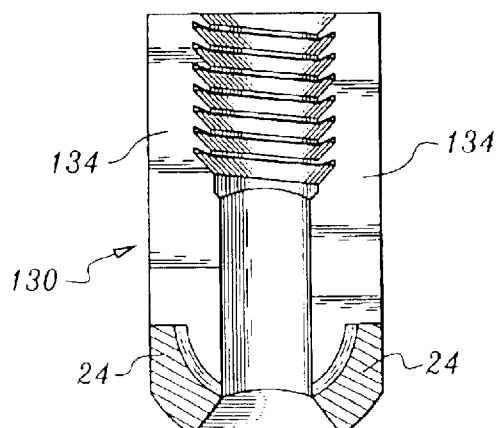
Fig. 13
Fig. 12

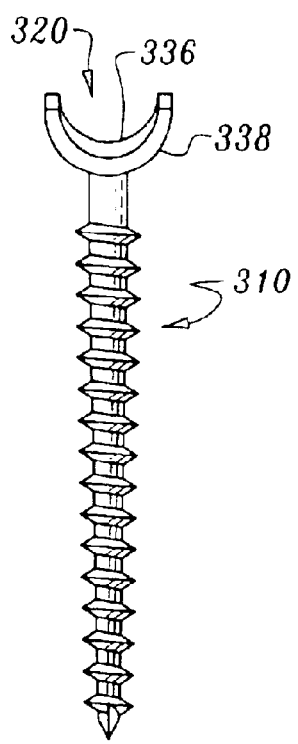
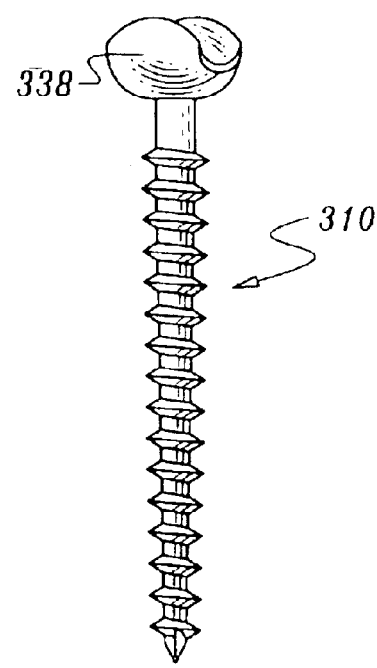
Fig. 26  Fig. 27
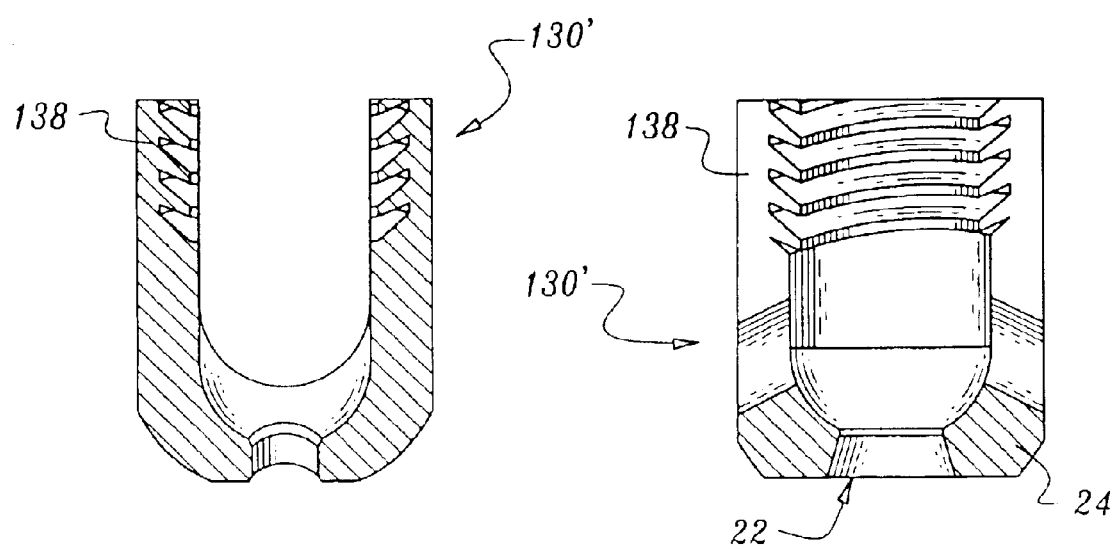
Fig. 28  Fig. 29

ORTHOPEDIC STABILIZATION DEVICE AND METHOD

FIELD OF THE INVENTION

The instant invention is directed generally to devices used by orthopedic surgeons to stabilize and align skeletal structures. More specifically, the instant invention includes a fastener capable of rotation about an axis within a supporting cup, the cup contoured to receive a rod therein and a means to fix the rod and rotationally oriented fastener in a fixed position.

BACKGROUND OF THE INVENTION

Orthopedic procedures involving stabilization of skeletal structure presently suffer from two common frailties: the first is the inability to orient the stabilizing structure for a multiplicity of common angulations and the second is the failure to provide a reliable thread portion which engages bone of the patient.

SUMMARY OF THE INVENTION

The instant invention provides the ability to address various skeletal components in a relational way by allowing articulation of the device in a multiplicity of angulations and to fasten to the skeletal structure to provide greater stabilization with an improved thread pattern which provides both axially compressive forces along the length of the fastener and radially inward drawing forces.

OBJECTS OF THE INVENTION

Accordingly, it is a primary object of the present invention to provide an orthopedic stabilization structure.

A further object of the present invention is to provide an improved threaded portion therefore.

A further object of the present invention is to accommodate a plurality of angulations when addressing a skeletal structure Viewed from a first vantage point, it is an object of the present invention to provide an orthopedic device, comprising, in combination: a fastener having a threaded body and a top portion provided with a saddle; a saddle having an upper face and a lower face; an upper face contoured to receive a rod thereon; and a lower face including a seating area for reception within a cup whereby said fastener can articulate within said cup.

These and other objects will be made manifest when considering the following detailed specification when taken in conjunction with the appended drawing figures.

BRIEF DESCRIPTION OF THE DRAWINGS

FIG. 4 shows the fastener and stabilization structure.
FIG. 5 is another view of FIG. 4.
FIG. 6 displays angulation of the FIG. 4 structure.
FIG. 7 details a bolt used in the structure.
FIG. 8 details the bolt receiving area.
FIG. 9 shows one side of the cup.
FIG. 10 shows an adjacent side (90 degrees) relative to FIG. 9, showing a diametrical slot.
FIG. 11 is a top view of FIGS. 9 and 10.
FIG. 12 is a bottom view of FIGS. 9 through 11.
FIG. 13 is a sectional view of FIG. 9 along lines 13—13.
FIG. 20 is a perspective of a clamp to be used with the FIG. 19 stem.
FIG. 26 is an alternative fastener to that which is shown in FIG. 1.
FIG. 27 is a perspective of FIG. 26.
FIG. 28 is a side section of a cup for use with FIGS. 26 and 27.
FIG. 29 is another side section of FIG. 28.

DESCRIPTION OF PREFERRED EMBODIMENTS

Figure 1:
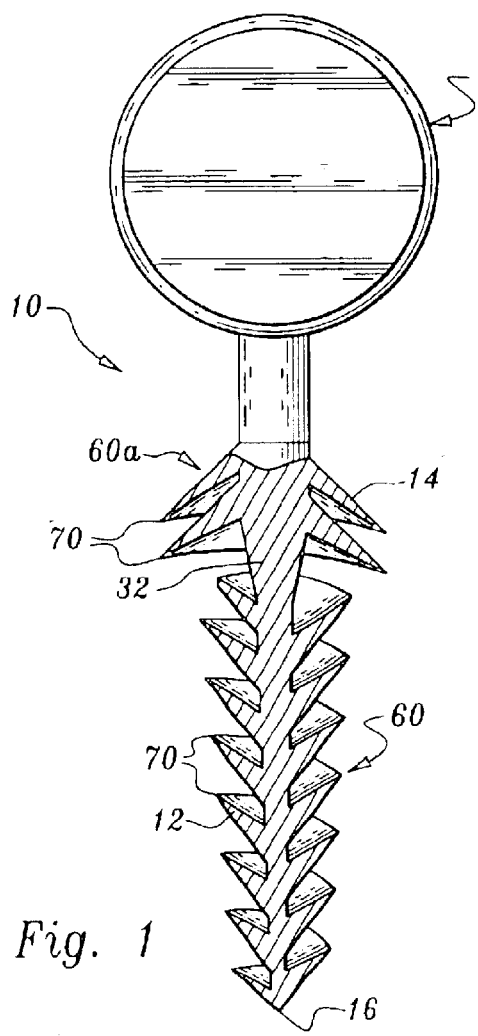
FIG. 1 is a top view of the fastener.

Considering the drawings, wherein like reference numerals denote like parts throughout the various drawing figures, reference numeral 100 is directed to the orthopedic stabilization device according to the present invention.

The device 100 allows a threaded fastener 10 to move about the arrow C as shown in FIG. 4 such that although the long axis of the threaded shaft is depicted as presently aligned, it can be rotated and skewed from a vertical long axis of a cup 130 as in FIG. 6. A rotational means 120 embodied as a disc has a cylindrical outer face 122 and planar top and bottom faces 124, 126. Thus, rotation about the arrow C occurs about a geometrical center 128. The disc 120 is integrally fixed to fastener 10. The rotational means 120 is constrained within a cup 130 having a central bore 132, an upper portion of which is provided with threads 111. In addition, a transverse slot 134 is cut along a diameter of the cup which allows slideable insertion therein of both the fastener 10 and integral disc 120 as well as a rod 136 transverse to a long axis of the cup 130. Please see FIGS. 9 through 16. The cup 130 is dimensioned such that the rotational means 120 is in tangential registry along one cylindrical face 122 with the rod 136. The threaded bore 132 receives a threaded fixing bolt 110 therewithin to press the rod 136 against the rotational means 120 to fix their relative relationship once appropriate orientation has occurred.

In its essence, the fastener 10 includes a threaded shaft 32 having a first thread pattern 12 at one end and a second thread pattern 14 at an opposite end. As shown in FIGS. 1 and 2, the first end thread pattern 12 terminates in a point 16 and the threads increase in diameter to form a thread pattern with its spiral increasing as it extends away from the point 16.

Figure 2:
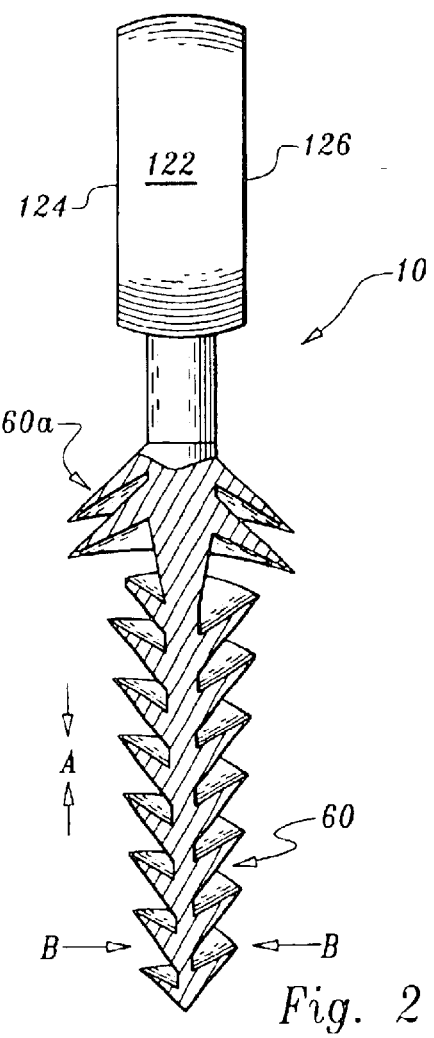
FIG. 2 is a side view of the fastener.

The second thread pattern 14 has a larger diameter but a similar thread contour which shall be discussed in detail infra. Preferably, the shaft 32 is of variable length and tapers and narrows from end 18 to point 16. Please see FIGS. 1 and 2.

A further nuance of the first and second thread patterns is that the first thread pattern 12 has a coarser thread than the second thread pattern 14 which is a finer thread. The point 16 is the point of initiation for insertion into a bone during an orthopedic procedure. To facilitate same, a pilot hole may be drilled in the bone but thereafter, because of the tapering nature of the first thread 12, this portion is thereafter self-threading. Notice that the crest 70 for both first and second thread patterns are sharp. This allows cutting into the bone which typically has a harder exterior than the interior. By providing a coarser thread pattern for the first thread 12, this thread will insert into the bone faster than the second thread pattern 14. As a consequence, when the bone begins to be engaged by the second thread pattern, an axial compression of the bone occurs along the direction of the two arrows A. In addition, because of the thread geometry, the threads will exert a radially inwardly directed force along the direction of the double-ended arrows B. Whereas in the prior art, conventional fasteners induced radially outwardly spreading (the opposite direction from arrow B), the instant invention provides radially inwardly or a drawing force B as well as the compressive force A.

The threads 60 of fastener 10 for threads 12 and 14 are actually one continuous helically wound thread which begins at the ends and spirals towards the medial portion of shaft 32 as it migrates from the ends. Please see FIG. 3.

The threads 60 include a sharpened crest 70 defining a major diameter 62 of the threads and a root 80 defining a minor diameter 64 of the threads 60. As shown in detail in FIG. 3, the threads 60 have an upper surface 66 which extends from a bottom edge 84 of the root 80 to the sharpened crest 70. The threads 60 also include a lower surface 68 which extends from a top edge 82 of the root 80 to the sharpened crest 70. Both the upper surface 66 and lower surface 68 angle toward the medial portion of the fastener as the surfaces 66, 68 extend from the root 80 to the crest 70.

In section, the surfaces 66, 68 extend linearly from the root 80 to the sharpened crest 70. However, as this contour is rotated helically about the threaded shaft 32 along with the threads 60, the upper surface 66 and lower surface 68 take on a curved surface appearance. This appearance is similar to that which would be formed by a linear section of the surface of a cone with a tip of the cone oriented downward and the cone rotated and translated upward along a central axis thereof. The upper surface 66 and lower surface 68 thus have a curved surface in three dimensions similar to that of a cone, but a linear character when viewed in section.

The upper surface 66 extends from the root 80 to the sharpened crest 70 at an upper surface angle α diverging from a reference plane orthogonal to the central long axis 2 of the fastener. The upper surface angle α is preferably 20° but could be any angle between 0° and 90°. The lower surface 68 extends from the root 80 to the sharpened crest 70 at a lower surface angle β with respect to the reference plane. The lower surface angle β is preferably 40° but could vary between 0° and 90°.

The upper surface angle α is preferably less than the lower surface angle β. In this way, the threads 60 are provided with greater thickness, and hence greater strength adjacent the minor diameter 64 than at the major diameter 62 and are thus more capable of bearing the loads experienced within the bone.

It is the angulation of the surfaces, especially upper surface 66 which encourages the radially inward force. When the upper and lower thread patterns are combined, axial compressive forces can be seen. Note the flat wall 54 of FIG. 3. This could replace point 16 and require a deeper pilot hole.

Figure 3:
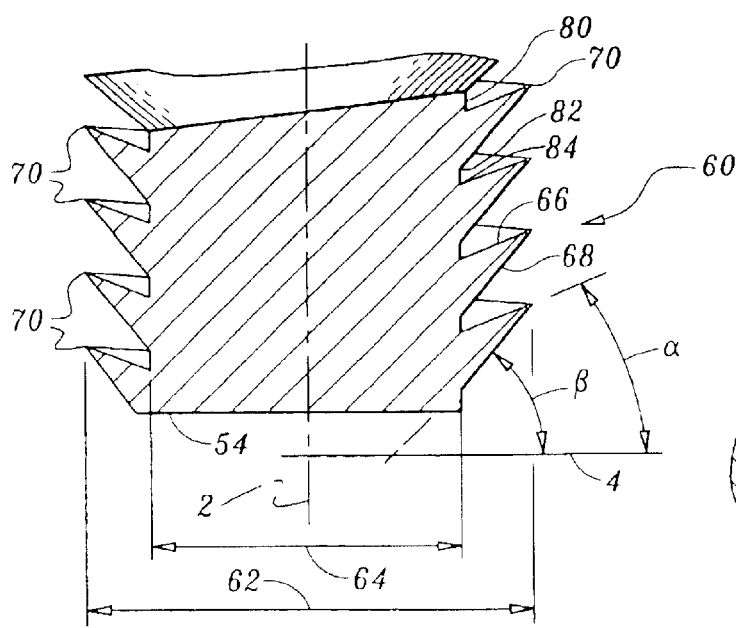
FIG. 3 is a sectional view of the fastener geometry.

The second thread portion 14 has the same FIG. 3 geometry except that the threads 60a are inverted, and as mentioned earlier are a finer thread (greater threads per inch axially) than the first thread portion 12. In other words FIG. 3 would be viewed upside down for threads 14.

Figure 3A:
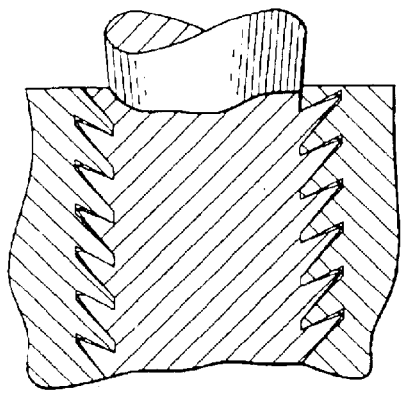
FIG. 3A shows FIG. 3 with a taper.
Figure 14:
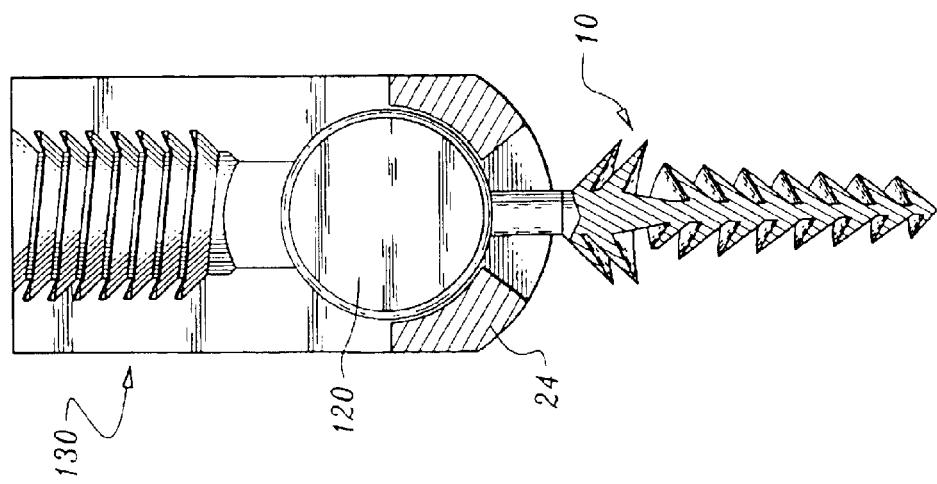
FIG. 14 is a sectional view similar to FIG. 4.
Figure 15:
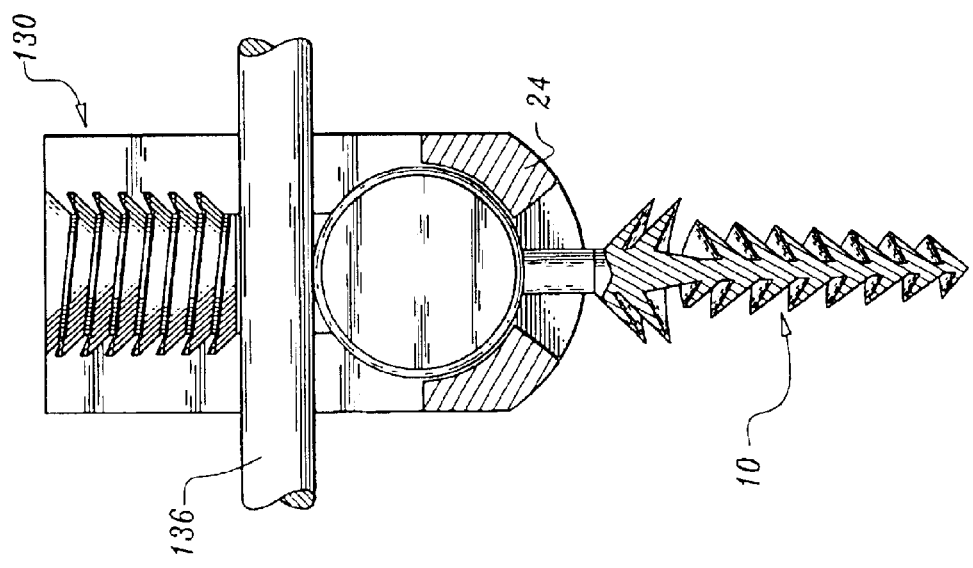
FIG. 15 adds a fastener and rod to FIG. 14.

FIG. 3A shows a section of thread with a pronounced taper. For thread pattern 14, FIG. 3A would be viewed upside down and with a reverse taper to that shown.

A bottom 129 of cup 130 (FIG. 4) has clearance 22 which extends within an included arc preferably approaching 90 degrees to allow a wide range of fastener 10 rotation about arrow C. Rotation beyond this clearance 22 is prevented by cup wall structure 24 that survives both the clearance aperture 22 and the slot 134 that runs diametrically down two sides of the substantially cylindrical cup 100. Free ends 138 of the cup 100 need the support a bolt 110 (FIG. 16) to: (first) press the rod 136 in place by (second) applying pressure to the disk 120 and retaining it by (third) uniting the free ends 138.

The threads 60 of the threaded bolt 110 (FIGS. 7 and 16) are actually one continuous helically wound thread which begins at the bottom 54 and spirals up to the top 52. While this single thread design is preferred, other arrangements including compound series of threads which wind helically together from the bottom 54 to the top 52 could also be utilized.

The threads 60 include a crest 170 defining a major diameter 62 of the threads and root 80 defining a minor diameter 64 of the threads 60. As shown in detail in FIG. 7, the threads 60 have an upper surface 66 which extends from a bottom edge 84 of the root 80 to the upper edge 72 of crest 170. The threads 60 also include a lower surface 68 which extends from a top edge 82 of the root 80 to a lower edge 74 of the crest 170. Both the upper surface 66 and lower surface 68 angle upwards as the surfaces 66, 68 extend from the root 80 to the crest 170. Both the crest 170 and root 80 exhibit a constant distance from the central axis 2 between the top edge 82 and the bottom edge 84. Compared to FIG. 3, crest 170 is blunt, while crest 70 is sharpened. Also, bolt 110 and thread 111 could have sharp contours like crest 70 (replacing crest 170) and vice versa.

In section, the surfaces 66, 68 extend linearly from the root 80 to the crest 170. However, as this contour is rotated helically about the threaded bolt 110 along with the threads 60, the upper surface 66 and lower surface 68 take on a curved surface appearance. This appearance is similar to that which would be formed by a linear section of the surface of a cone with a tip of the cone oriented downward and the cone rotated and translated upward along a central axis thereof. The upper surface 66 and lower surface 68 thus have a curved surface in three dimensions similar to that of a cone, but a linear character when viewed in section.

The upper surface 66 extends from the root 80 to the crest 170 at an upper surface angle α diverging from a reference plane 4 orthogonal to the central axis 2. The upper surface angle α is preferably 20 degrees but could be any angle between 0 degrees and 90 degrees. The lower surface 68 extends from the root 80 to the crest 170 at a lower surface angle β with respect to the reference plane 4. The lower surface angle β is preferably 40 degrees but could vary between 0 degrees and 90 degrees.

The upper surface angle α is preferably less than the lower surface angle β such that a thickness of the threads 60 at the crest 170 is less than a thickness of the threads 60 between adjacent roots 80. In this way, the threads are provided with greater thickness, and hence greater strength adjacent the minor diameter 64 than at the major diameter 62 and are thus more capable of bearing the loads experienced within the threaded bore 132.

Referring now to FIG. 8, details of the threaded bore 132 on free ends 138 are shown. The bore is preferably substantially complemental in form to the threaded shaft of the bolt 110. The bore includes threads T. The thread geometry of the bolt 110 and threads T draw free ends 136 of cup 130 together along arrow D.

Figure 17:
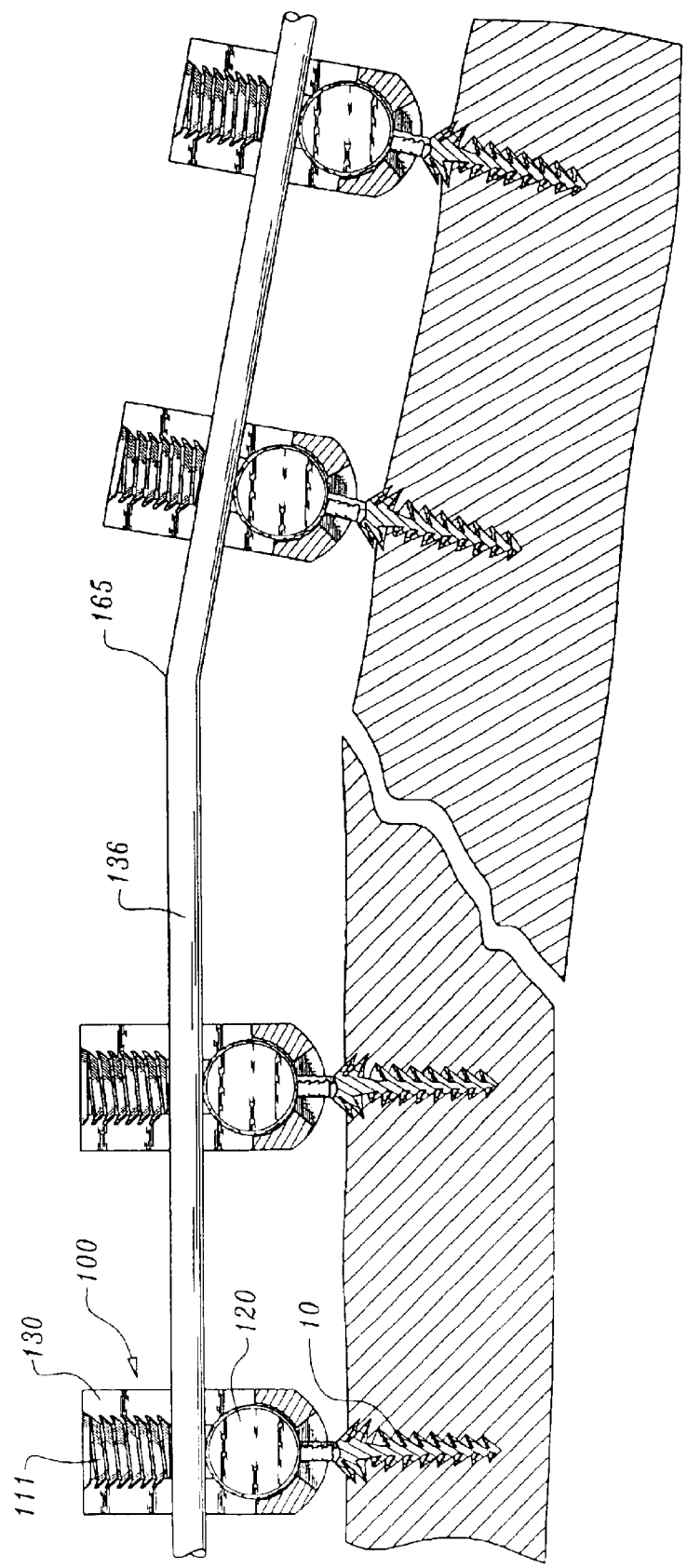
FIG. 17 shows the device deployed by way of example.

FIG. 17 shows a fractured bone and the device 100 being applied. The fasteners 10 with discs 120 and the cups 130 are located such that the fasteners 10 are located in the bone, but the disc can rotate within clearance 22 as described. Recall the threads 12, 14 axially compress and radially inwardly drawing in the bone. Next the rod 136 is placed within the slots 134 of the cups 130.

The rod is shown as having a bend 165 to demonstrate the system's versatility. Next the bolts 110 are threaded into threads 111 in the free ends 138 of the cups 130. As the bolts 110 bear on rod 136, the rod 136, disc 120 and fastener 10 become rigid. The free ends 138 also draw together tightly.

Figure 18:
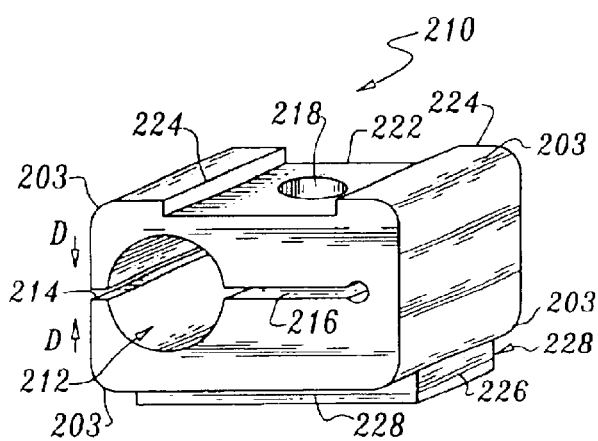
FIG. 18 shows an alternative thread pattern.

FIG. 18 is a view similar to FIG. 4 showing an embodiment where the first and second thread patterns have conventional geometry but the second thread pattern has a greater thread pitch density, defining finer threads than the first thread pattern.

Figure 16:
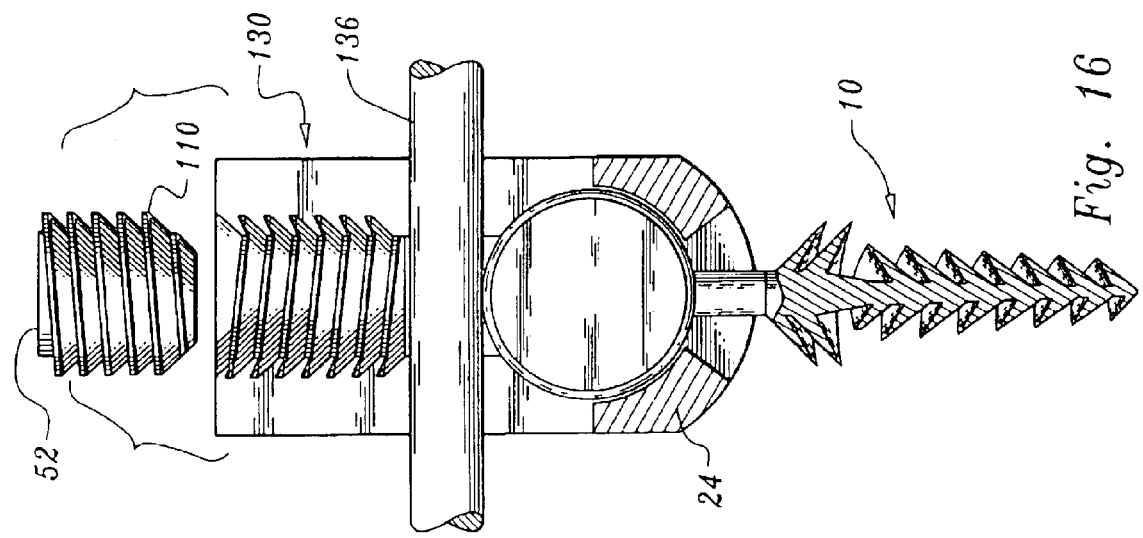
FIG. 16 adds a fixing bolt to FIG. 15.
Figure 19A:
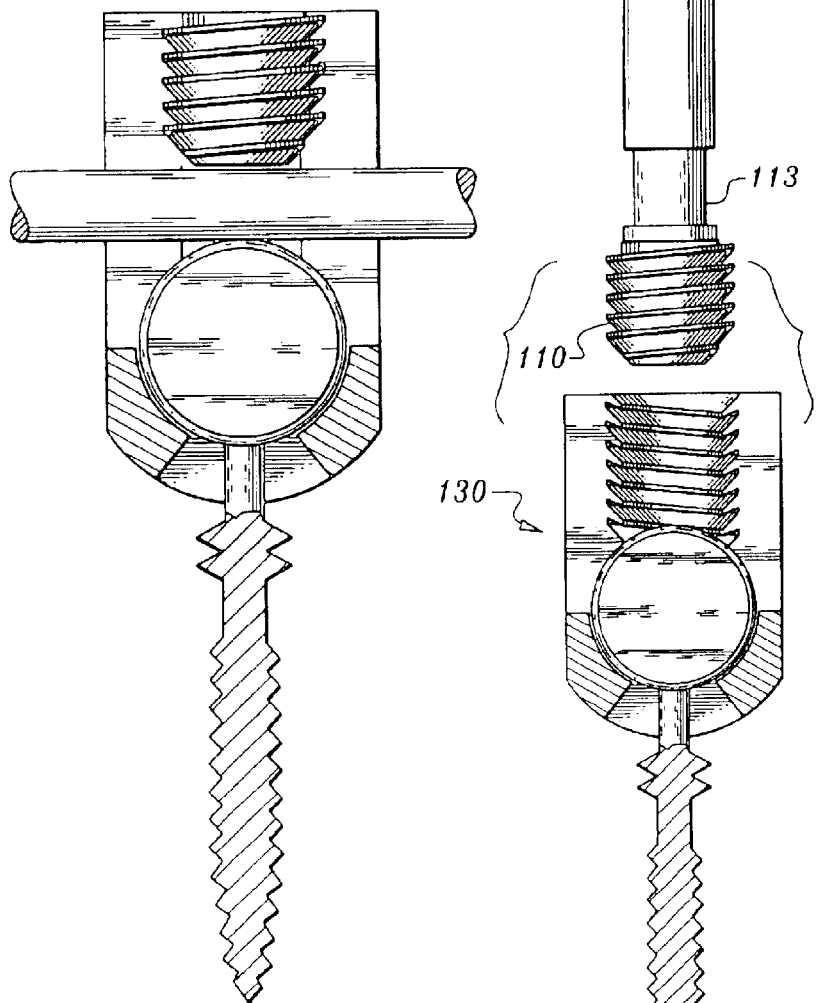
FIGS. 19A and B show the bolt of the earlier drawings modified to include a stem.
Figure 19B:
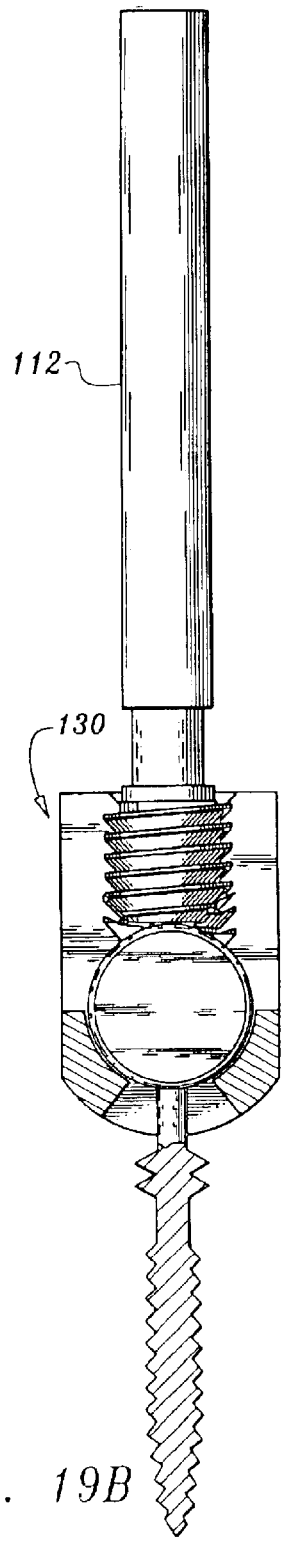
Figure 21:
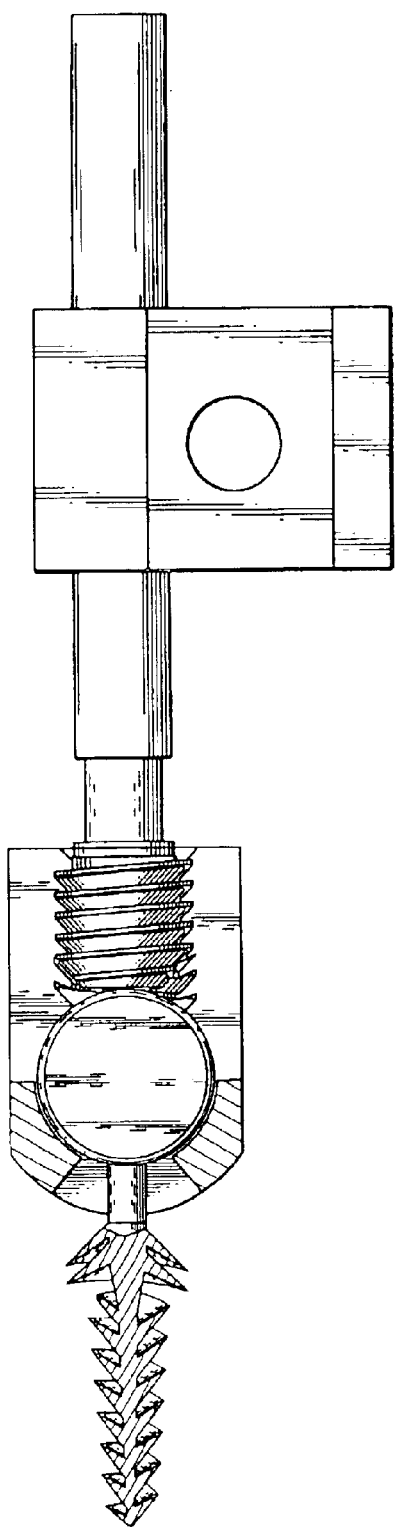
FIG. 21 shows the clamp mounted on the stem.

FIGS. 19A and B are similar to FIG. 16 except that the bolt 110 includes an elongate stem 112 projecting from a top of the bolt 110 and projects from the cup 130. The stem 112 may include a necked down area 113 adjacent bolt 110. Stem is preferably cylindrical while the necked down area 113 can be faceted to rotate stem 112 with a tool.

Figure 22:
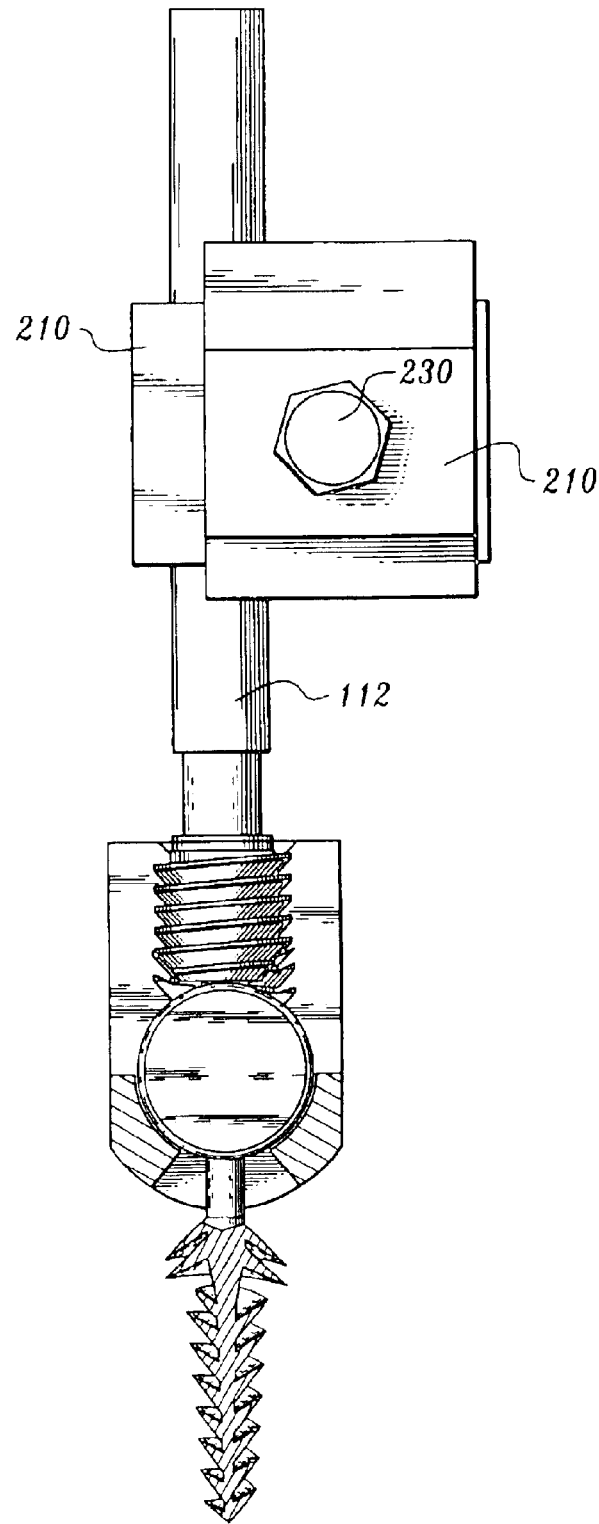
FIG. 22 shows two clamps on the stem from one side.
Figure 23:
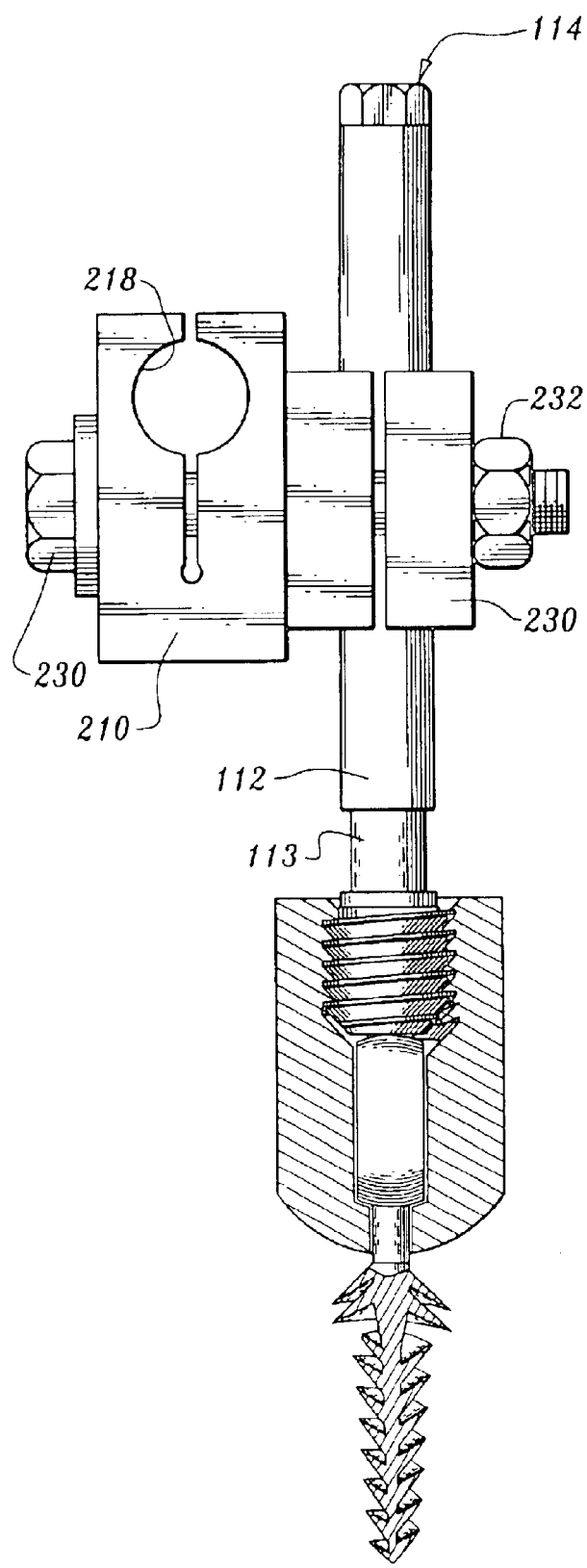
FIG. 23 shows two clamps on the stem from another side.

FIG. 20 is a perspective view of a stem clamp 210 which fixes to stem 112. Clamp 210 includes a cylindrical bore 212 dimensioned to receive stem 112 and includes a slit 214 on an outer wall and is diametrically aligned with a groove 216 extending into the clamp body. Slit and groove collectively cooperate with a bore 218 passing through clamp 210 perpendicular to groove 216. When slit 214 and groove 216 and drawn together along arrow D, the stem 112 is fixed in position. Clamp 210 is substantially box shaped and includes a top surface 222 which is planar except for two outboard raised edgewalls 224 oriented parallel to the stem bore 212. The edgewalls 224 in conjunction with top surface 222 define a receiving slot dimensioned to receive a projection 226 similar to the rectangular projection 226 shown in FIG. 20 on the bottom surface. The projection 226 thus includes projection walls leading to the body of the clamp 210 such that the span between the edgewalls 224 equals the span of the projection between the projection walls 228. Note the projection 226 is offset from the top surface 222 (and its recess defined by edgewalls 224) by 90 degrees. This allows plural clamping blocks 210 to be stacked as shown in FIGS. 22 and 23 in a stabile manner. A bolt 230, passing through plural bores 218 holds the clamps in place via a nut 232. Corners 203 of clamp 210 may be chamfered.

Figure 25:
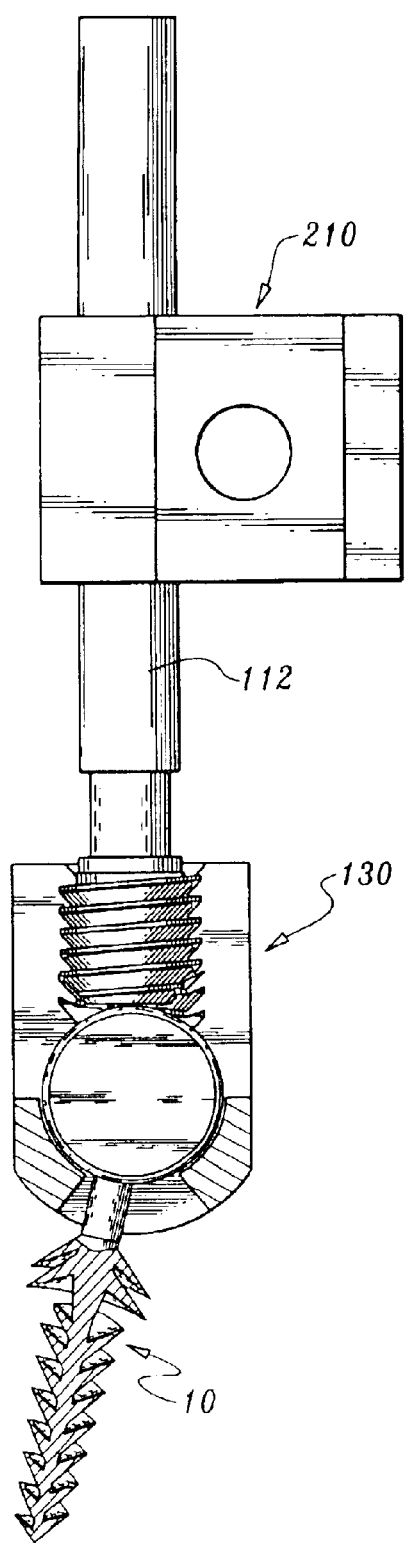
FIG. 25 illustrates angulation of FIGS. 22 and 23.
Figure 24:
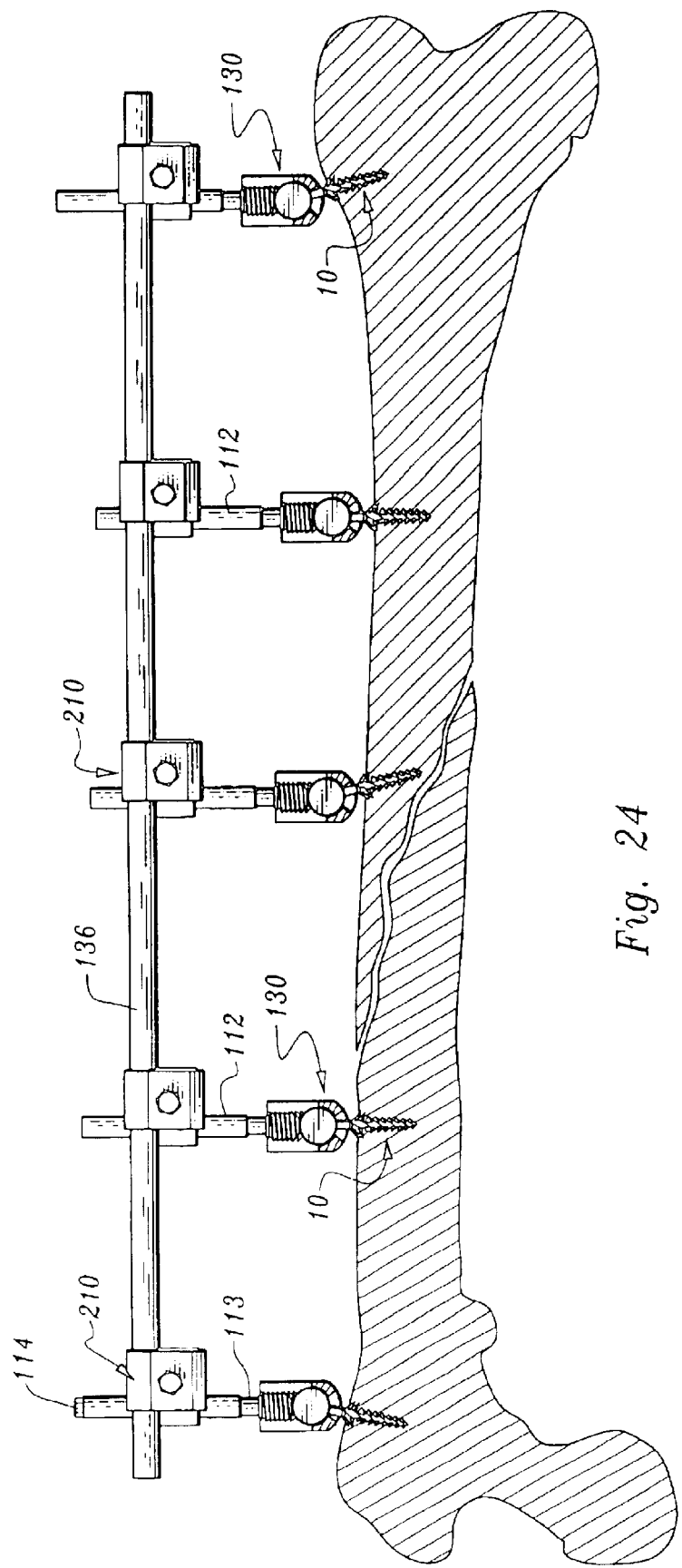
FIG. 24 shows a deployment of FIGS. 18 through 23.

FIG. 24 shows how this alternative embodiment uses the stem as an extension to accommodate the rod 136 discussed in FIG. 17. Instead of rod 136 being interposed between disc 120 and bolt 110, the rod is received through one bore 218 of one clamp 210 mated as shown in FIG. 23, while a second bore receives the stem 112. This embodiment favors external deployment of rod 136 external the body of a patient. To use the FIG. 24 device, the fasteners 10 (with discs 120 and cups 130) are threaded along the bore. The stem 112 having the bolt 110 integral therewith is next threaded into the cup 130. The stems 112 are not yet tightened, allowing the cups to angulate (e.g. FIG. 25) to follow the bone contour. The clamps 210 are next positioned on the stems 112 in pairs along with rod 136. The stems 112 are next tightened against disc 120 to fix the cups 130 by pressing the bolt 110 against the cylindrical outer face 122 of disc 120. Note that the geometry of the disc 120 and its placement in slot 134 prevents the fastener from working loose in the bone, particularly with the thread geometry 12, 14 discussed above. Next the rod 136, the clamps 210 and stems 112 are fixed in position by bolts 230 and nuts 232. At this point, the fracture (or other orthopedic anomaly) has been stabilized. While the necked down portion 113 may be faceted, the end 114 of stem 112 may have a drive head in lieu of or in addition to facets on stem 112.

Figure 30:
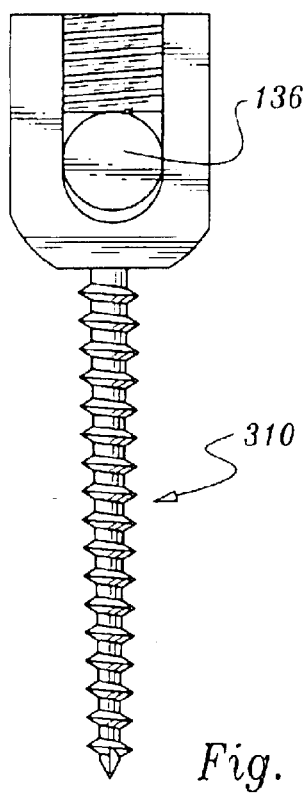
FIG. 30 shows the FIG. 26 fastener deployed in the FIG. 28 cup with a fixing rod.
Figure 31:
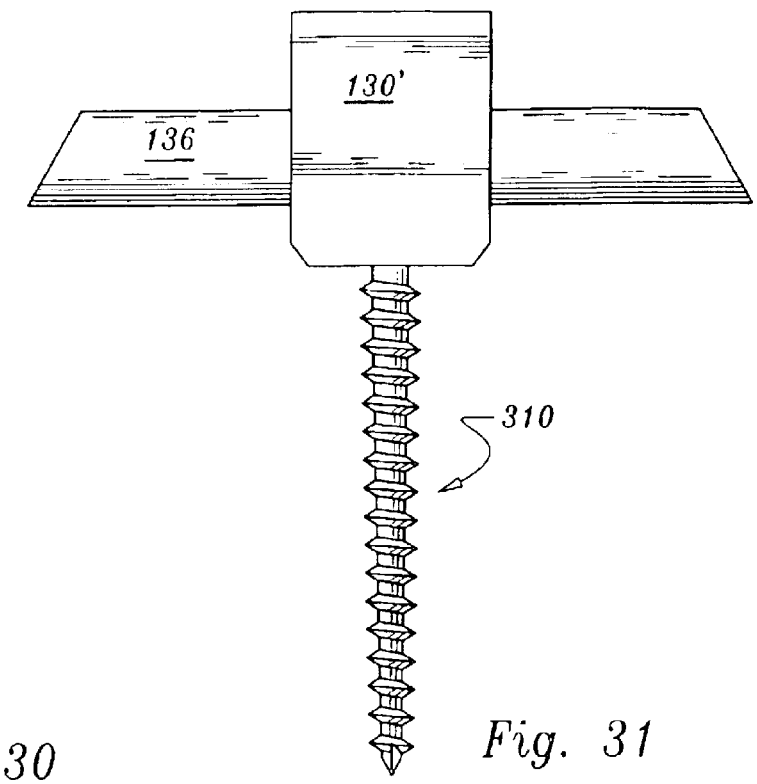
FIG. 31 is a second view of FIG. 30.
Figure 32:
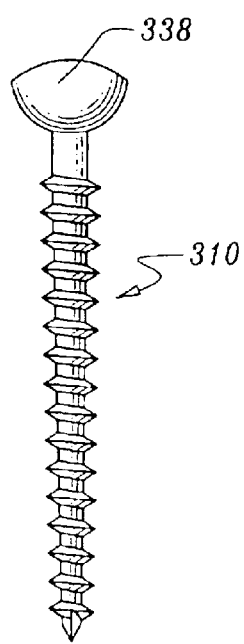
FIG. 32 is a side view of FIG. 26.
Figure 33:
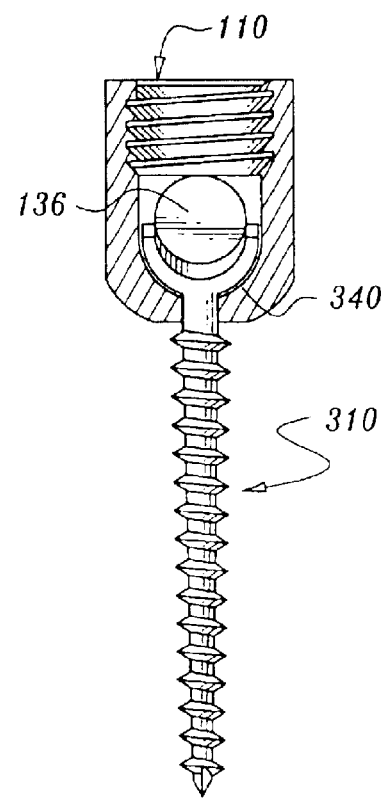
FIG. 33 is a view of FIG. 30 with a threaded bolt deployed.
Figure 34:
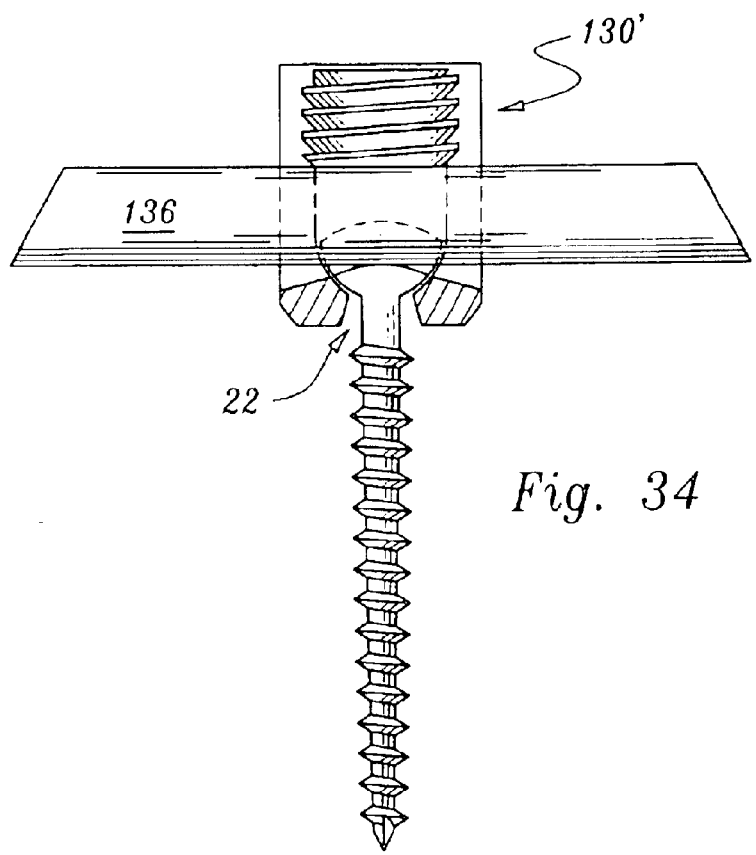
FIG. 34 shows FIG. 33 from the side.
Figure 35:
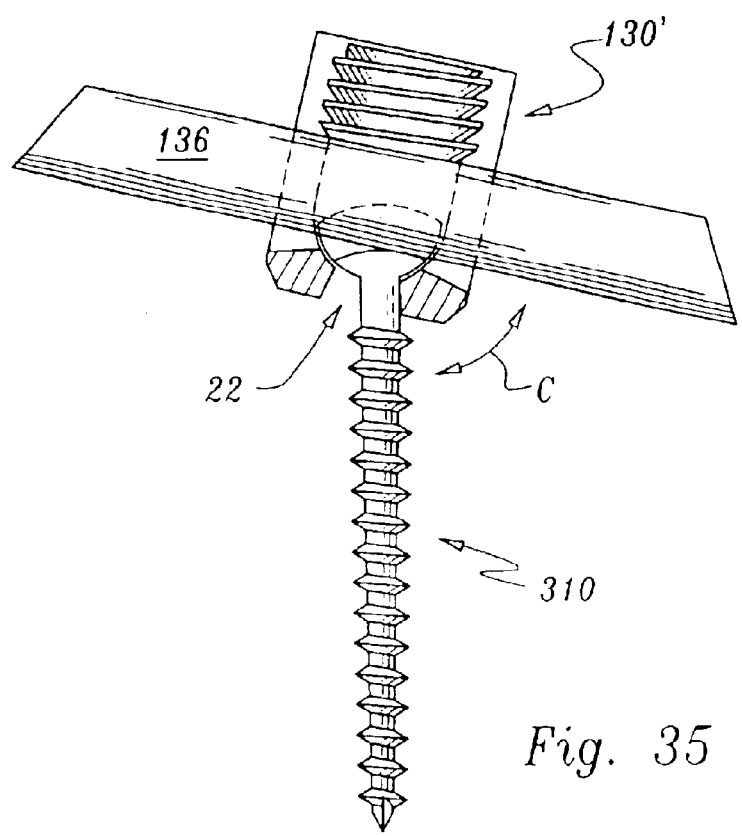
FIG. 35 shows FIG. 34 angulated.

FIGS. 26, 27 and 32 show a front, perspective and side view, respectively of an alternative fastener 310 compared to FIG. 1. Similarities with earlier embodiments will not be belabored. Most notably, the rotational means 120 of FIG. 1 has been replaced with a saddle 320. The saddle 320 has a radiused top surface 336 dimensioned to receive 2 rod 136 (FIGS. 30 and 33) in tangential registry about approximately half the circumference of the rod 136. Thus, the radius of curvature of the saddle's top surface 336 matches the radius of curvature of rod 136. Compared to the FIG. 4 arrangement, the saddle 320 enjoys greater surface contact with the rod 136. This results in less work being needed to hold the rod 136 and fastener 310 in a fixed position because of the greater contact area. Also, the overall length of the fastener is reduced resulting in a shorter, more compact overall height of the device as shown for example in FIG. 33 (compared to FIG. 6) because a major portion of disc 120 has been substituted by the lower profile saddle 320 which in effect is an outer arc of a circle of the FIG. 6 disk. As a consequence, cup 130' can also be made correspondingly shorter. FIGS. 27 and 32 show outer shoulders 338 of the saddle which have a curvature complimental to its seat 340 (FIG. 33) in the cup 130'. As before, clearance 22 allows relative rotation between the fastener 310 and the rod 136 and cup 130' about arrow C.

Moreover, having thus described the invention, it should be apparent that numerous structural modifications and adaptations may be resorted to without departing from the scope and fair meaning of the instant invention as set forth hereinabove and as described hereinbelow by the claims.

I claim:

1. An orthopedic device, comprising, in combination:

a threaded shaft said shaft having one terminus provided with rotational means about a single axis transverse to a long axis of said threaded shaft and means to prohibit all other rotation, a cup having an upper end with interior threads and having a lower rotational means receiving area dimensioned to allow rotation of said threaded shaft about said one terminus and about a said single axis transverse to said long axis of said threaded shaft and means to prohibit all other rotation, said cup having a transverse slot, a rod passing through said slot and abutting a saddle on said rotational means in proximate tangential registry, and bolt means threaded to said cup's interior threads to fix said rod and said threaded shaft into a fixed position relative to said cup wherein said threaded shaft has first and second thread patterns thereon wherein said threaded shaft first and second thread patterns have differing thread pitch, such that said second thread pattern has finer threads than said first thread pattern wherein said thread patterns have crests which are axially offset from their respective roots, inducing a radially inward directed force.

2. The device of claim 1 wherein said first and second thread crests face each other inducing compressive force axially.

3. A method for supporting a skeletal structure, the steps including:

deploying a plurality of fasteners within a plurality of support cups;

screwing the fasteners into a bone to be mended such that the bone is subjected to both axially compressive and radially inward forces relative to the fastener;

deploying a support rod within the support cups;

orienting the cups relative to the rod so the rod abuts saddles on the fasteners;

and fixing the rod and fasteners together by inducing a radially inward force on the cups.

4. An orthopedic device, comprising, in combination:

a fastener having a threaded body and a top portion provided with a saddle;

said saddle having an upper face and an uninterrupted lower face;

said upper face contoured to receive a cylindrical rod thereon;

said upper face is in tangential registry with approximately one half a circumference of said rod; and said lower face including a seating area for reception within a cup whereby shoulders of said fastener are in tangential registry with and can articulate within said cup, said cup having a seat complemental to said shoulders, and said cup having upwardly projecting inwardly threaded free ends provided with angle threads, and a bolt having angled threads disposed within said cup threads to provide radially inward forces to obviate the need for a collar.

5. An orthopedic stabilization device, comprising, in combination:

a threaded shaft having both axial and radial bone engaging compressive threads, said shaft having a free end terminating in a saddle constrained within a cup having a recess complemental to said saddle to permit relative rotation of said cup and said shaft about a geometrical center of said saddle, a rod received within said cup and a tangential registry with said saddle, and means to hold said rod, cup and saddle in fixed relationship.

* * * * *